United States Patent
Nagano et al.

(10) Patent No.: US 6,872,846 B2
(45) Date of Patent: Mar. 29, 2005

(54) PROCESS FOR PREPARATION OF TERTIARY ALCOHOL ESTERS

(75) Inventors: Shinya Nagano, Himeji (JP); Hiroshi Shimojitosho, Osaka (JP)

(73) Assignee: Daicel Chemical Industries, Ltd., Sakai (JP)

( * ) Notice: Subject to any disclaimer, the term of this patent is extended or adjusted under 35 U.S.C. 154(b) by 0 days.

(21) Appl. No.: 10/399,516

(22) PCT Filed: Nov. 13, 2001

(86) PCT No.: PCT/JP01/09896

§ 371 (c)(1),
(2), (4) Date: Apr. 17, 2003

(87) PCT Pub. No.: WO02/42252

PCT Pub. Date: May 30, 2002

(65) Prior Publication Data

US 2004/0015006 A1 Jan. 22, 2004

(30) Foreign Application Priority Data

Nov. 24, 2000 (JP) .................................... 2000-358463

(51) Int. Cl.$^7$ .............................................. C07C 69/74
(52) U.S. Cl. ...................................... 560/116; 560/231
(58) Field of Search ................................ 560/116, 231

(56) References Cited

U.S. PATENT DOCUMENTS 6,248,920 B1   6/2001   Takechi et al.

FOREIGN PATENT DOCUMENTS

| EP | 1 043 298 A1 | 10/2000 |
| EP | 1 070 699 A1 | 1/2001 |

OTHER PUBLICATIONS

English translation of Japanese Unexamined Patent Application Publication No. 9–052864 (Feb. 25, 1997).

*Primary Examiner*—Paul J. Killos
(74) *Attorney, Agent, or Firm*—Birch, Stewart, Kolasch & Birch, LLP

(57) ABSTRACT

The production process of the present invention comprises a step of allowing a carboxylic acid derivative represented by the formula (1):

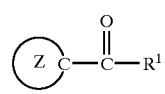

(1)

wherein ring Z is a monocyclic or polycyclic non-aromatic or aromatic ring, and $R^1$ is a halogen atom or a group represented by the formula (2):

—OR    (2)

wherein R is a hydrogen atom or a hydrocarbon group, to react with an organometallic compound represented by the formula (3):

$R^2$-M    (3)

wherein $R^2$ is a hydrocarbon group, and M is a metallic atom which may have a ligand, or the formula (4):

-MgY    (4)

wherein Y is a halogen atom,
and a carboxylic acid halide represented by the formula (5):

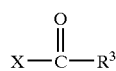

(5)

wherein $R^3$ is a hydrocarbon group or a heterocyclic group, and X is a halogen atom,
to yield the tertiary alcohol ester represented by the formula (6):

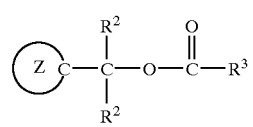

(6)

wherein Z, $R^2$ and $R^3$ have the same meanings as defined above.

According to the present invention, a tertiary alcohol compound having a tertiary carbon combined with a ring group can be easily and efficiently produced from carboxylic acid derivative which is comparatively cheap and readily available.

10 Claims, No Drawings

PROCESS FOR PREPARATION OF TERTIARY ALCOHOL ESTERS

This application is the national phase under 35 U.S.C. § 371 of PCT International Application No. PCT/JP01/09896 which has an International filing date of Nov. 13, 2001, which designated the United States of America.

TECHNICAL FIELD

The present invention relates to a process for producing a tertiary alcohol ester, and in more detail to a process for producing a tertiary alcohol ester having a ring such as a non-aromatic ring, which is useful as a monomer of a functional polymer, such as a photosensitive resin, and others.

BACKGROUND ART

An ester of a tertiary alcohol having a non-aromatic ring group such as an alicyclic hydrocarbon group with a polymerizable unsaturated carboxylic acid is allowed to function as an acid-responsive compound because a part of alcohol is eliminated from the ester in the presence of an acid to become soluble in alkali. Therefore the ester focused in recent years is a compound as a monomer for a functional polymer such as a photosensitive resin, particularly a resist resin.

Generally, a tertiary alcohol ester can be synthesized by reacting an acid or an acid halide with a corresponding tertiary alcohol. A common acid-responsive tertiary alcohol ester, because of an acid-responsiveness thereof, is synthesized by reacting an acid halide with a corresponding tertiary alcohol under an amine such as triethyl amine.

However, it has been hard to efficiently produce a tertiary alcohol ester having a tertiary carbon atom bonding with a non-aromatic ring such as a bulky alicyclic hydrocarbon ring by the above-mentioned technique from the corresponding tertiary alcohol. More concretely, when reacting an acryl halide with a tertiary alcohol, which has a tertiary carbon atom bonding with a bulky non-aromatic ring, under an amine such as triethylamine, it has been difficult to efficiently obtain a corresponding acrylic acid ester because there have been problems; many polymeric compounds of a corresponding acrylic acid ester are generated, a concentration of substrate can't be increased because of much deposition of a salt and so on. Furthermore, in case of reacting a methacrylic acid halide with the alcohol having a tertiary carbon atom bonding with a bulky non-aromatic ring under an amine such as triethylamine, a desired methacrylic acid ester is hardly produced due to the low reactivity thereof.

Thus an efficient esterification of the tertiary alcohol having a branched chain thereof bonding with a non-aromatic ring such as a bulky alicyclic hydrocarbon ring is hardly carried out due to the following reasons; a low reactivity according to a bulkiness thereof and an easy elimination of an ester portion caused by having an acid-responsiveness. Such problem can be also caused when a carboxylic acid portion is not only an unsaturated carboxylic acid but also a saturated aliphatic carboxylic acid, an aromatic carboxylic acid and so on. Further, the above problem can be caused in case of not only the tertiary alcohol having a branched chain bonding with a non-aromatic ring but also a tertiary alcohol bonding with an aromatic ring.

Furthermore, to add to the above problems in the esterification, an alcohol compound used as a raw material is desired to produce separately and therefore the following problems are also caused; a complication of operation and a time demerit in a production.

DISCLOSURE OF INVENTION

Accordingly, an object of the present invention is to provide a process for easily and efficiently producing a tertiary alcohol ester compound having a tertiary carbon atom, which bonds with a ring group, from a carboxylic acid derivative which is comparatively cheap and can be obtained easily.

The present inventors made intensive investigations to achieve the above object, and found that when a specific organometallic compound and a carboxylic acid halide are used, a tertiary alcohol ester having a tertiary carbon atom bonding with a ring group can be produced easily and efficiently from a carboxylic acid derivative which can be obtained easily. The present invention has been accomplished based on these findings.

Specifically, the present invention provides a process for producing a tertiary alcohol ester, which comprises a step of allowing a carboxylic acid derivative represented by the formula (1):

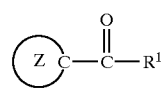　(1)

wherein ring Z is a monocyclic or polycyclic non-aromatic or aromatic ring, and $R^1$ is a halogen atom or a group represented by the formula (2):

　(2)

wherein R is a hydrogen atom or a hydrocarbon group, to react with an organometallic compound represented by the formula (3):

　(3)

wherein $R^2$ is a hydrocarbon group, and M is a metallic atom which may have a ligand, or the formula (4):

　(4)

wherein Y is a halogen atom,
and with a carboxylic acid halide represented by the formula (5):

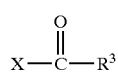　(5)

wherein $R^3$ is a hydrocarbon group or a heterocyclic group, X is a halogen atom,
to yield the tertiary alcohol ester represented by the formula (6):

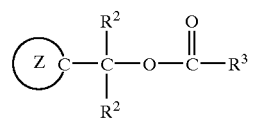　(6)

wherein Z, $R^2$ and $R^3$ have the same meanings as defined above.

The ring Z may be a bridged cyclic ring containing 2 to 4 rings such as norbornane ring, bornane ring, adamantane ring, bicyclooctane ring, tricyclo[5.2.1.0$^{2,6}$]decane ring or decalin ring. The ring Z, for example, may have a substituent such as a halogen atom, an alkyl group, a hydroxyl group which may be protected by a protecting group or an amino group which may be protected by a protecting group.

Preferably, $R^1$ is a halogen atom, a $C_{1-4}$ alkoxy group or others. $R^2$ includes, for example, a $C_{1-6}$ alkyl group, a $C_{3-12}$ cycloalkyl group, a $C_{6-20}$ aryl group or others. $R^3$ includes, for example, a hydrocarbon group having a polymerizable unsaturated group such as vinyl group, 1-propenyl group or isopropenyl group, or others.

BEST CODE FOR CARRYING OUT THE INVENTION

[Carboxylic Acid Derivatives]

In the carboxylic acid derivative shown by the above formula (1), a halogen atom represented by $R^1$ includes chlorine atom, bromine atom, iodine atom and others.

In the group shown by the above formula (2), a hydrocarbon group represented by R includes an aliphatic hydrocarbon group, an alicyclic hydrocarbon group, an aromatic hydrocarbon group and a group conjugated by two or more groups thereof.

The above aliphatic hydrocarbon group can be a $C_{1-10}$ aliphatic hydrocarbon group (a linear or branched chain alkyl group, a linear or branched alkenyl group and a linear or branched alkynyl group) such as methyl group, ethyl group, propyl group, isopropyl group, butyl group, isobutyl group, s-butyl group, t-butyl group, pentyl group, hexyl group, octyl group, decyl group, vinyl group, allyl group and 2-propynyl group, and others. The preferable aliphatic hydrocarbon group is a $C_{1-6}$ (particularly $C_{1-4}$) aliphatic hydrocarbon group.

The alicyclic hydrocarbon includes, for example, 3 to 8 membered-alicyclic hydrocarbon group (cycloalkyl group, cycloalkenyl group and others) such as cyclopentyl group and cyclohexyl group, and others.

The aromatic hydrocarbon group includes, for example, $C_{6-14}$ aromatic hydrocarbon group such as phenyl group and naphtyl group, and others. The group combined by two or more groups which have a different sort of hydrocarbon group includes, for example, about $C_{7-16}$ aralkyl group such as benzyl group and 2-phenylethyl group, and others.

The above hydrocarbon group may have a substituent. The substituent, if don't interfere a reaction, particularly isn't limited and includes, for example, a halogen atom, a substituted oxy (or thio) group (for example methoxy group, methylthio group, methoxyethoxy group, 2-(trimethylsilyl) ethoxy group, benzyloxy group and others), acyl group (for example bezoyl group and others) and so on.

The preferable $R^1$ includes a halogen atom, a linear or branched $C_{1-4}$ alkoxy group and others.

The ring Z is a monocyclic or polycyclic non-aromatic or aromatic ring. The above non-aromatic ring includes an alicyclic hydrocarbon ring (a non-aromatic hydrocarbon ring) and a non-aromatic hetero ring. The alicyclic hydrocarbon ring includes a monocyclic hydrocarbon ring and a polycyclic hydrocarbon ring [a spirohydrocarbon ring, a ring-assembling hydrocarbon ring, a bridged cyclic hydrocarbon ring (including a condensed cyclic hydrocarbon ring)], and the non-aromatic hetero ring includes a monocyclic hetero ring and a polycyclic hetero ring (a bridged cyclic hetero ring).

The monocyclic hydrocarbon ring includes, for example, a $C_{3-12}$ cycloalkane ring such as cyclopentane ring, cyclohexane ring, cycloheptane ring and cyclooctane ring, a $C_{3-12}$ cycloalkene ring such as cyclohexene ring, and so on. The spirohydrocarbon ring includes, for example, a $C_{5-16}$ spirohydrocarbon ring such as spiro[4.4]nonane, spiro[4.5] decane and spirobicyclohexane ring, and others. The ring-assembling hydrocarbon ring includes, for example, a ring-assembling hydrocarbon ring including a $C_{3-12}$ cycloalkane ring such as bicyclohexane and biperhydronaphthalene ring.

The bridged cyclic hydrocarbon ring includes, for example, a two-cyclic hydrocarbon ring such as pinane ring, bornane ring, norpinane ring, norbornane ring and bicyclooctane ring (such as bicyclo[2.2.2]octane ring and bicyclo[3.2.1]octane ring), a three-cyclic hydrocarbon ring such as homobledane, adamantane, tricyclo[5.2.1.0$^{2,6}$] decane and tricyclo[4.3.1.1$^{2,5}$]undecane, a four-cyclic hydrocarbon ring such as tetracyclo[4.4.0.1$^{2,5}$.1$^{7,10}$] dodecane and perhydro-1,4-methano-5,8-methanonaphthalene ring, and so on.

The bridged cyclic hydrocarbon ring includes a ring corresponding to a hydrogenated product of a dimer of diene [for example, a hydrogenated product of a dimer of cycloalkadiene, for example, such as cyclopentadiene, cyclohexadiene and cycloheptadiene (for example, such as perhydro-4,7-methanoindene), a dimer of butadiene (vinylcyclohexene) or a hydrogenated product thereof and others] and so on.

Further, the bridged cyclic hydrocarbon ring is, for example, a condensed-cyclic hydrocarbon ring which is a ring condensed with two or more 5- to 8-membered cycloalkanes such as perhydronaphthalene (decalin) ring, perhydroanthracene ring, perhydrophenanthrene ring, perhydroacenaphthene ring, perhydrofluorene ring, perhydroindene ring or perhydrophenalene ring.

The preferred bridged cyclic hydrocarbon ring is, for example, norbornane ring, bornane ring, adamantane ring, bicyclooctane ring, tricyclo[5.2.1.0$^{2,6}$]decalin ring, decalin ring and others.

The monocyclic non-aromatic hetero ring is, for example, an oxygen-atom-containing hetero ring such as oxolane ring, oxane ring, oxepane ring or oxocane ring, a nitrogen-atom containing hetero ring such as perhydroazepine ring and so on. The polycyclic non-aromatic hetero ring is a bridged cyclic hetero ring or others.

Further, the above aromatic ring includes an aromatic hydrocarbon ring, an aromatic hetero ring and so on. The aromatic hydrocarbon ring is, for example, a monocyclic or polycyclic aromatic hydrocarbon ring such as benzene ring, naphthalene ring, anthracene ring, phenanthrene ring or phenalene ring. The aromatic hetero ring is, for example, a monocyclic or polycyclic aromatic hetero ring, such as furan ring, thiophene ring, pyridine ring, pyridazine ring, pyrimidine ring, pyrazine ring, quinoline ring, isoquinoline ring, quinazoline ring, quinoxaline ring, acridine ring and phenazine ring, which contains one or several hetero atoms such as oxygen atom, nitrogen atom or sulfur atom.

The preferable ring Z is a polycyclic non-aromatic ring (a hydrocarbon ring or a hetero ring) and particularly a bridged cyclic ring (a bridged cyclic hydrocarbon ring or a bridged cyclic hetero ring) containing 2 to 4 rings such as adamantane ring is more preferred.

The ring Z may have a substituent. The substituent isn't particularly limited if don't interfere to the reaction. The examples of typical substituents are a halogen atom (such as bromine, chlorine and fluorine atom), an alkyl group (a $C_{1-4}$ alkyl group such as methyl group, ethyl group, butyl group and t-butyl group, and others), a hydroxyl group protected by a protecting group, an amino group protected by a protecting group and so on.

The protecting group of hydroxyl group is a common protecting group in a field of organic synthesis, which is, for example, an alkyl group (e.g. a $C_{1-4}$ alkyl group such as methyl group and t-butyl group, and others), a cycloalkyl group (e.g. cyclohexyl group and others), an aralkyl group (e.g. benzyl group and others), a substituted methyl group (e.g. methoxymethyl group, methothiomethyl group, benzyloxymethyl group, t-butoxymethyl group, 2-methoxyethoxymethyl group and others), a substituted ethyl group (e.g. 1-ethoxyethyl group, 1-methyl-1-methoxyethyl and others), an acyl group (e.g. a $C_{1-6}$ aliphatic acyl group such as formyl group, acetyl group, propionyl group, butyryl group, isobutyryl group, valeryl group, pivaloyl group; acetacetyl group; an aromatic acyl group such as benzoyl group and naphthoyl group; and others), an alkoxycarbonyl group (e.g. a $C_{1-4}$ alkoxycarbonyl group such as methoxycarbonyl group, ethoxycarbonyl group and t-butoxycarbonyl group, and others), an aralkyloxycarbonyl group (e.g. benzyloxycarbonyl group, p-methoxybenzyloxycarbonyl group and others). The preferable protecting group of hydroxyl group includes a $C_{1-4}$ alkyl group, a substituted methyl group, a substituted ethyl group, an acyl group, a $C_{1-4}$ alkoxycarbonyl group and so on.

A protecting group of the above amino group is, as described about the above protecting group of hydroxyl group, an alkyl group, a cycloalkyl group, an aralkyl group, an acyl group, an alkoxycarbonyl group, aralkyloxycarbonyl group and so on. The preferable protecting group of amino group includes a $C_{1-4}$ alkyl group, a $C_{1-6}$ aliphatic acyl group, an aromatic acyl group, a $C_{1-4}$ alkoxycarbonyl group and others.

[Organometallic Compounds (Organometallic Reagent)]

In an organometallic compound represented by the above formula (3), the metallic atom M is, for example, an alkali metal atom such as lithium, a transition metal atom such as cerium, titanium and copper and so on. The metallic atom may have a ligand. The ligand is, for example, a halogen atom such as chlorine atom, an alkoxy group such as isopropoxy group, a dialkylamino group such as diethylamino group, a cyano group, an alkyl group, an alkali metal atom such as lithium atom, and so on.

$R^2$ means a hydrocarbon group and is, for example, a $C_{1-6}$ aliphatic hydrocarbon group (e.g. an alkyl group, an alkenyl group, an alkynyl group) such as methyl, ethyl, propyl, isopropyl, butyl, isobutyl, s-butyl and t-butyl; a $C_{3-12}$ alicyclic hydrocarbon group (e.g. a cycloalkyl group and a cycloalkenyl group) such as cyclopropyl group, cyclobutyl group, cyclopentyl group, cyclohexyl group, cyclohexenyl group, cyclooctyl group, cyclododecyl group; a $C_{6-20}$ aromatic hydrocarbon group (e.g. an aryl group) such as phenyl group, and so on.

$R^2$ may have a substituent. The substituent is, for example, the same as the substituent described in the R. The preferable $R^2$ includes a $C_{1-6}$ alkyl group, a $C_{3-12}$ cycloalkyl group, a $C_{6-20}$ aryl group and others, and particularly a $C_{1-4}$ alkyl group, a $C_{5-6}$ cycloalkyl group, a phenyl group and so on.

In the formula (4) described above, a halogen atom represented by Y is chlorine, bromine and iodine atom.

The typical examples of organometallic compounds represented by the above formula (3) are an organic titanium compound (an ate complex of organic titanium and others) such as dimethyldiisopropoxytitanium; an organic magnesium compound (Grignard reagent and others) such as methyl magnesium bromide, ethyl magnesium bromide and butyl magnesium bromide; an organic lithium compound such as methyl lithium and butyl lithium; and so on. The organic magnesium compound can be used by combining with a copper halide.

The amount used of organometallic compound represented by the above formula (3) is, for example, 2 to 4 moles per one mole of the carboxylic acid derivative represented by the above formula (1), preferably about 2 to 2.5 moles.

[Carboxylic Acid Halide]

In the carboxylic acid halide represented by the above formula (5), $R^3$ is a hydrocarbon group or a heterocyclic group.

The hydrocarbon group includes an aliphatic hydrocarbon group, an alicyclic hydrocarbon group, an aromatic hydrocarbon group and a group combined by these two or more groups. The aliphatic hydrocarbon group is, for example, a linear or branched chain alkyl group (e.g. a $C_{1-20}$ alkyl group) such as methyl group, ethyl group, propyl group, isopropyl group, butyl group, isobutyl group, s-butyl group, t-butyl group, pentyl group, hexyl group, octyl group and decyl group; a linear or branched chain alkenyl group (e.g. a $C_{2-20}$ alkenyl group) such as vinyl group, allyl group, isopropenyl group, 1,2-dimethyl-1-propenyl group, 1-butenyl group and 1-hexenyl group; a linear or branched chain alkynyl group (e.g. a $C_{2-20}$ alkynyl group) such as 2-propynyl group; and so on.

An alicyclic hydrocarbon group is, for example, a 3-to-20-membered cyclic hydrocarbon group (e.g. a cycloalkyl group, a cycloalkenyl group and a bridged-cyclic hydrocarbon group) such as cyclopentyl group, cyclohexyl group, cyclohexenyl group, cyclooctyl group and cyclododecyl group, and so on.

An aromatic hydrocarbon group is, for example, a $C_{6-20}$ aromatic hydrocarbon group such as phenyl group and naphtyl group, and soon. Further, a group combined by several different sort of hydrocarbon groups is, for example, an about $C_{7-21}$ aralkyl group, such as benzyl group, 2-phenylethyl group, and so on.

A hetero cyclic group includes, for example, an about 5-to-6-membered cyclic aromatic or non-aromatic hetero ring having at least one sort of about 1 to 4 hetero atoms such as nitrogen atom, oxygen atom and sulfur atom, and a condensed ring which is produced by condensing the hetero ring to other aromatic or non-aromatic hydrocarbon ring or hetero ring.

These hydrocarbon group and hetero cyclic ring group may have various sort of substituent as far as don't prevent a reaction.

The preferable $R^3$ includes a hydrocarbon group having a polymerizable unsaturated group. The typical hydrocarbon group having a polymerizable unsaturated group is, for example, an alkenyl group (particularly 1-alkenyl group) such as vinyl group, 1-propenyl group and isopropenyl group.

The halogen atom represented by X is, for example, chlorine atom, bromine atom and iodine atom.

The typical examples of carboxylic acid halide represented by the formula (5) are an acrylic acid halide such as acrylic acid chloride, a methacrylic acid halide such as methacrylic acid chloride, a crotonic acid halide such as crotonic acid chloride, and other unsaturated carboxylic acid halides, and so on.

An amount used of carboxylic acid halide represented by the formula (5) can be selected, for example, from a range of about 1 to 5 mole based on one mole of the carboxylic acid derivative represented by the formula (1). Still more, when the carboxylic acid derivative represented by the formula (1) is a carboxylic acid halide (namely when $R^1$ is a halogen atom), the amount used of carboxylic acid halide represented by the formula (5) is preferably about 1 to 2 moles, and more preferably about 1 to 1.5 moles based on one mole of the carboxylic acid derivative. Further, when the carboxylic acid derivative represented by the formula (1) is a carboxylic acid ester (namely when $R^1$ is the group represented by the formula (2)), an amount used of the carboxylic acid halide represented by the formula (5) is preferably about 2 to 4 moles, and more preferably about 2 to 2.5 moles based on one mole of the carboxylic acid derivative.

[Reaction]

The method of the present invention can be usually carried out by first allowing the carboxylic acid derivative represented by the formula (1) to react with the organometallic compound represented by the formula (3) in an organic solvent and then the generated reactive intermediate to react with the carboxylic acid halide represented by the formula (5).

The organic solvent may be an inert solvent to the reaction and, for example, an ether such as diethyl ether, 1,2-dimethoxyethane and tetrahydrofuran, and an aliphatic hydrocarbon such as heptane, hexane and octane can be used.

The reaction temperature can be properly selected, for example, in a range of about –100° C. to 150° C. according to a reaction component. For example, in the organometallic compound represented by the above formula (3), when M is a metallic atom (e.g. lithium), the reaction temperature is, for example, about –100° C. to 30° C. Still more, when a compound represented by the formula (3) wherein M is the group represented by the formula (4) is used, the reaction temperature is, for example, about 0° C. to 150° C., preferably about 20° C. to 100° C.

The reaction can be carried out by a common method such as a batch, a semi-batch and a continuous system. Generally, the method is that the organometallic compound represented by the formula (3) (or a solution containing this compound) is added step by step into a solution containing the carboxylic acid derivative represented by the formula (1) and then the carboxylic acid halide represented by the formula (5) (or a solution containing this compound) is added step by step into the resulting solution.

Still more, the tertiary alcohol ester (6), having two $R^2$s which are different from each other in one molecular, can be obtained by using the two sorts of organometallic compounds (3) having a different $R^2$ respectively. For example, in the solution containing the carboxylic acid derivative represented by the formula (1), one of the two sorts of organometallic compounds (3) having a different $R^2$ respectively is added, then another is added and next the carboxylic acid halide represented by the formula (5) is added to produce the above unsymmetrical tertiary alcohol ester.

After the reaction, the resulting reaction mixture is quenched with water or others if necessary, and then the desired reaction product can be obtained by a separating-purification method such as a filtration, a concentration, a extraction, a washing, a distillation, a crystallization, a recrystallization or a column chromatography.

Thus the obtained tertiary alcohol ester is useful for a monomer of functional polymeric compounds, and an intermediate product of fine chemicals. Particularly the compound which enables to produce a free carboxylic acid by eliminating a part of alcohol due to an acid can be used for a raw material of monomer of photosensitive resin as an acid-responsive compound.

Industrial Applicability

The method of the present invention can provide the efficiency process of producing by one-pot the tertiary alcohol ester compound, which has a cyclic group bonded to a tertiary carbon atom, by using a comparatively cheap and easily obtainable carboxylic acid derivative. More concretely the issues, such as a low reactivity, a production of polymeric compound and a limitation of material concentration, in the conventional production method using an alcohol compound as a raw material are solved to be able to produce a much amount of desired product in a short time. Further, because producing the alcohol compound separately is not needed, complicated processes such as purifications can be simplified.

EXAMPLES

The present invention will now be described in more detail with reference to several examples below, which are not intended to limit the scope of the invention.

Example 1

Production of 1-(1'-adamantyl)-1-methylethyl acrylate from 1-adamantane carboxylic acid butyl ester (methyl lithium method)

In a 300 ml flask equipped with a stirrer and a thermometer, 1-adamantane carboxylic acid butyl ester (10 g/42.31 mmol) and THF (tetrahydrofuran; 50 ml) were placed and stirred under nitrogen gas stream. The liquid temperature was cooled to –40° C. and 1.40 M ether solution (66.49 ml/93.08 mmol) of methyl lithium was added therein dropwise for one hour and the mixture was further maintained at 0° C. for 3 hours. Into this solution, 30 ml of THF solution of acrylic acid chloride (8.42 g/93.08 mmol) was added dropwise for one hour and the resulting mixture was further maintained at room temperature for two hours. According to the analysis of the resulting reaction mixture by the high performance liquid chromatography, 1-(1'-adamantyl)-1-methyethyl acrylate (yield; 72.2%) represented by the formula (6a) was generated.

50 ml of n-hexane was added to the reaction mixture and the resulting mixture was washed once respectively by each of pure water, 10 weight % aqueous solution of sodium carbonate and 10 weight % aqueous solution of sodium chloride. Then the solvent was removed under a reduced pressure and purified with the silicagel column chromatography to obtain 1-(1'-adamantyl)-1-methyethyl acrylate (7.26 g/yield; 69.1%) as the desired compound.

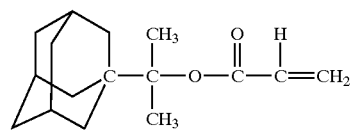

(6a)

Example 2

Production of 1-(1'-adamantyl)-1-methylethyl acrylate from 1-adamantane carboxylic acid butyl ester (methyl magnesium bromide method)

In a 300 ml flask equipped with a stirrer and a thermometer, 1-adamantane carboxylic acid butyl ester (10 g/42.31 mmol) and 50 ml of THF were placed and stirred under nitrogen gas stream. While the liquid temperature was controlled at 60° C., 1.0 M THF solution (93.08 ml/93.08 mmol) of methyl magnesium bromide was added dropwise for one hour and the mixture was further maintained at 60° C. for 3 hours. Then while the liquid temperature was controlled at 50° C., THF (30 ml) solution of acrylic acid chloride (8.42 g/93.08 mmol) was added dropwise into this solution for one hour and the resulting mixture was further maintained at 50° C. for two hours. According to the analysis of the resulting reaction mixture by the high performance liquid chromatography, 1-(1'-adamantyl)-1-methyethyl acrylate (yield; 57.5%) represented by the above formula (6a) was generated.

50 ml of n-hexane was added to the reaction mixture and the resulting mixture was washed once respectively by each of pure water, 10 weight % aqueous solution of sodium carbonate and 10 weight % aqueous solution of sodium chloride. Then the solvent was removed under a reduced pressure and purified with the silicagel column chromatography to obtain 1-(1'-adamantyl)-1-methyethyl acrylate (5.58 g/yield; 53.1%) as the desired compound.

Example 3

Production of 1-(1'-adamantyl)-1-methylethyl acrylate from 1-adamantane carboxylic acid chloride (methyl lithium method)

The reaction of EXAMPLE 1 was repeated, except that 1-adamantane carboxylic acid chloride was used instead of 1-adamantane carboxylic acid butyl ester. According to the analysis of the resulting reaction mixture by the high performance liquid chromatography, 1-(1'-adamantyl)-1-methyethyl acrylate (yield; 74.4%) represented by the formula (6a) was generated. 50ml of n-hexane was added to the reaction mixture and the resulting mixture was washed once respectively by each of pure water, 10 weight % aqueous solution of sodium carbonate and 10 weight % aqueous solution of sodium chloride. Then the solvent was removed under a reduced pressure and purified with the silicagel column chromatography to obtain 1-(1'-adamantyl)-1-methyethyl acrylate (7.44 g/yield; 70.8%) as the desired compound.

Example 4

Production of 1-(1'-adamantyl)-1-methylethyl acrylate from 1-adamantane carboxylic acid chloride (methyl magnesium bromide method)

The reaction of EXAMPLE 2 was repeated, except that 1-adamantane carboxylic acid chloride was used instead of 1-adamantane carboxylic acid butyl ester. According to the analysis of the resulting reaction mixture by the high performance liquid chromatography, 1-(1'-adamantyl)-1-methyethyl acrylate (yield; 60.1%) represented by the formula (6a) was generated. 50 ml of n-hexane was added to the reaction mixture and the resulting mixture was washed once respectively by each of pure water, 10 weight % aqueous solution of sodium carbonate and 10 weight % aqueous solution of sodium chloride. Then the solvent was removed under a reduced pressure and purified with the silicagel column chromatography to obtain 1-(1'-adamantyl)-1-methyethyl acrylate (5.93 g/yield; 56.4%) as the desired compound.

Example 5

Production of 1-(1'-adamantyl)-1-methylethyl methacrylate from 1-adamantane carboxylic acid butyl ester (methyl lithium method)

The reaction of EXAMPLE 1 was repeated, except that methacrylic acid chloride was used instead of acrylic acid chloride. According to the analysis of the resulting reaction mixture by the high performance liquid chromatography, 1-(1'-adamantyl)-1-methyethyl methacrylate (yield; 85.1%) represented by the following formula (6b) was generated. 50 ml of n-hexane was added to the reaction mixture and the resulting mixture was washed once respectively by each of pure water, 10 weight % aqueous solution of sodium carbonate and 10 weight % aqueous solution of sodium chloride. Then the solvent was removed under a reduced pressure and purified with the silicagel column chromatography to obtain 1-(1'-adamantyl)-1-methyethyl methacrylate (9.04 g/yield; 81.4%) as the desired compound.

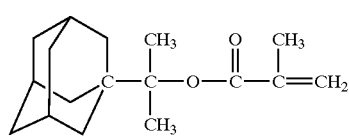

(6b)

Example 6

Production of 1-(1'-adamantyl)-1-methylethyl methacrylate from 1-adamantane carboxylic acid butyl ester (methyl magnesium bromide Method)

The reaction of EXAMPLE 2 was repeated, except that methacrylic acid chloride was used instead of acrylic acid chloride. According to the analysis of the resulting reaction mixture by the high performance liquid chromatography, 1-(1'-adamantyl)-1-methyethyl methacrylate (yield; 72.1%) represented by the formula (6b) was generated. 50 ml of n-hexane was added to the reaction mixture and the resulting mixture was washed once respectively by each of pure water, 10 weight % aqueous solution of sodium carbonate and 10 weight % aqueous solution of sodium chloride. Then the solvent was removed under a reduced pressure and purified with the silicagel column chromatography to obtain 1-(1'-adamantyl)-1-methyethyl methacrylate (7.59 g/yield; 68.4%) as the desired compound.

Example 7

Production of 1-(1'-adamantyl)-1-methylethyl methacrylate from 1-adamantane carboxylic acid chloride (methyl lithium method)

The reaction of EXAMPLE 3 was repeated, except that methacrylic acid chloride was used instead of acrylic acid chloride. According to the analysis of the resulting reaction mixture by the high performance liquid chromatography, 1-(1'-adamantyl)-1-methyethyl methacrylate (yield; 86.2%) represented by the formula (6b) was generated. 50 ml of n-hexane was added to the reaction mixture and the resulting mixture was washed once respectively by each of pure water, 10 weight % aqueous solution of sodium carbonate and 10 weight % aqueous solution of sodium chloride. Then the solvent was removed under a reduced pressure and purified with the silicagel column chromatography to obtain 1-(1'-adamantyl)-1-methyethyl methacrylate (9.16 g/yield; 82.5%) as the desired compound.

Example 8

Production of 1-(1'-adamantyl)-1-methylethyl methacrylate from 1-adamantane carboxylic acid chloride (methyl magnesium bromide method)

The reaction of EXAMPLE 4 was repeated, except that methacrylic acid chloride was used instead of acrylic acid chloride. According to the analysis of the resulting reaction mixture by the high performance liquid chromatography, 1-(1'-adamantyl)-1-methyethyl acrylate (yield; 74.2%) represented by the formula (6b) was generated. 50 ml of n-hexane was added to the reaction mixture and the resulting mixture was washed once respectively by each of pure water, 10 weight % aqueous solution of sodium carbonate and 10 weight % aqueous solution of sodium chloride. Then the solvent was removed under a reduced pressure and purified with the silicagel column chromatography to obtain 1-(1'-adamantyl)-1-methyethyl methacrylate (7.88 g/yield; 71.0%) as the desired compound.

Example 9

Production of 1-(1'-(3'-(2"-methoxyethoxymethyl)oxy)adamantyl)-1-methyl ethyl methacrylate from 1-(3-(2'-methoxyethoxymethyl)oxy)adamantane carboxylic acid butyl ester (methyl lithium method)

The reaction of EXAMPLE 5 was repeated, except that 1-(3-(2'-methoxyethoxymethyl)oxy)adamantane carboxylic acid butyl ester was used instead of 1-adamantane carboxylic acid butyl ester. According to the analysis of the resulting reaction mixture by the high performance liquid chromatography, 1-(1'-(3'-(2"-methoxyethoxymethyl)oxy)adamantyl)-1-methyl ethyl methacrylate (yield; 78.2%) represented by the following formula (6c) was generated. The resulting reaction mixture was washed once respectively by each of pure water, 10 weight % aqueous solution of sodium carbonate and 10 weight % aqueous solution of sodium chloride. Then the solvent was removed under a reduced pressure and purified with the silicagel column chromatography to obtain 1-(1'-(3'-(2"-methoxyethoxymethyl)oxy)adamantyl)-1-methyl ethyl methacrylate (11.43 g/yield; 73.7%) as the desired compound.

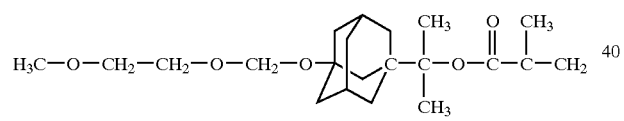

(6c)

Comparative Example 1

Production of 1-(1'-adamantyl)-1-methylethyl acrylate from 1-(1'-adamantyl)-1-methylethanol (triethyamine method)

In a 3 l flask equipped with a stirrer and a thermometer, 1-(1'-adamantyl)-1-methylethanol (125 g/643 mmol), methoxy phenol (0.125 g/1.0 mmol), triethylamine (130 g/1290 mmol) and toluene (1750 ml) were placed and stirred under nitrogen gas stream. Over a water bath, a solution of toluene (350 ml) of acrylic acid chloride (87.3 g/965 mmol) was added dropwise for one hour and the mixture was further maintained for one hour. According to the analysis of the resulting reaction mixture by the high performance liquid chromatography, 1-(1'-adamantyl)-1-methyethyl acrylate (yield; 56.4%) represented by the formula (6a) was generated. According to the further analysis, the following result was noticed that though 1-(1'-adamantyl)-1-methylethanol of the raw material was not almost remained, a much amount of polymerized compound of 1-(1'-adamantyl)-1-methyethyl acrylate which is the desired compound was generated.

Comparative Example 2

Production of 1-(1'-adamantyl)-1-methylethyl acrylate from 1-(1'-adamantyl)-1-methylethanol (sodium hydride method)

In a 300 ml flask equipped with a stirrer and a thermometer, sodium hydride (1.36 g/56.61 mmol) and 14 ml of THF were placed and stirred under nitrogen gas stream. By using a dropping funnel, THF (100 ml) solution of 1-(1'-adamantyl)-1-methylethanol (10 g/51.46 mmol) was added dropwise and the mixture was further stirred for 3 hours under reflux. Over a water bath, THF (20 ml) solution of acrylic acid chloride (5.12 g/56.61 mmol) was added dropwise for one hour by using a dropping funnel into the solution and the resulting mixture was further maintained at room temperature for 5 hours. According to the analysis of the resulting reaction mixture by the high performance liquid chromatography, 1-(1'-adamantyl)-1-methylethanol which is the raw material was almost remained and desired 1-(1'-adamantyl)-1-methyethyl acrylate was not generated.

Comparative Example 3

Production of 1-(1'-adamantyl)-1-methylethyl acrylate from 1-(1'-adamantyl)-1-methylethanol (acrylic acid method)

In a 300 ml flask equipped with a stirrer, a thermometer and dean-stark apparatus, 1-(1'-adamantyl)-1-methylethanol (10 g/51.46 mmol), methoxyphenol (0.10 g/0.8 mmol), p-toluene sulfonic acid-one hydrate (0.489 g/2.57 mmol), acrylic acid (5.56 g/77.19 mmol) and 100 ml of toluene were placed and the mixture was stirred for 2 hours under reflux while air stream was introduced. According to the analysis of the resulting reaction mixture by the high performance liquid chromatography, isopropenyladamantane represented by the formula (7) was almost generated in stoichiometry and 1-(1'-adamantyl)-1-methyethyl acrylate which is desired was not generated.

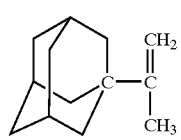

(7)

Comparative Example 4

Production of 1-(1'-adamantyl)-1-methylethyl methacrylate from 1-(1'-adamantyl)-1-methylethanol (triethylamine method)

The reaction of COMPARATIVE EXAMPLE 1 was repeated, except that methacrylic acid chloride was used instead of acrylic acid chloride. According to the analysis of the resulting reaction mixture by the high performance liquid chromatography, 1-(1'-adamantyl)-1-methylethanol which is the raw material was almost remained and 1-(1'-adamantyl)-1-methyethyl acrylate which is desired was not generated.

Comparative Example 5

Production of 1-(1'-adamantyl)-1-methylethyl methacrylate from 1-(1'-adamantyl)-1-methylethanol (sodium hydride method)

The reaction of COMPARATIVE EXAMPLE 2 was repeated, except that methacrylic acid chloride was used instead of acrylic acid chloride. According to the analysis of the resulting reaction mixture by the high performance liquid chromatography, 1-(1'-adamantyl)-1-methylethanol which is the raw material was almost remained and 1-(1'-adamantyl)-1-methyethyl acrylate which is desired was not generated.

What is claimed is:

1. A process for producing a tertiary alcohol ester, comprising a step of allowing a carboxylic acid derivative represented by the formula (1):

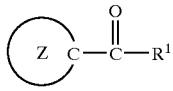
(1)

wherein ring Z is a monocyclic or polycyclic non-aromatic or aromatic ring, and $R^1$ is a halogen atom or a group represented by the formula (2):

—OR (2)

wherein R is a hydrogen atom or a hydrocarbon group, to react with an organometallic compound represented by the formula (3):

$R^2$-M (3)

wherein $R^2$ is a hydrocarbon group, and M is a metallic atom which may have a ligand, or the formula (4):

-MgY (4)

wherein Y is a halogen atom,
and a carboxylic acid halide represented by the formula (5):

(5)

wherein $R^3$ is a hydrocarbon group or a heterocyclic group, X is a halogen atom,
to yield the tertiary alcohol ester represented by the formula (6):

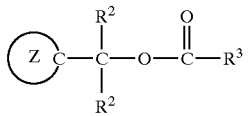
(6)

wherein Z, $R^2$ and $R^3$ have the same meanings as defined above.

2. The process for producing a tertiary alcohol ester according to claim 1, wherein the ring Z is a bridged cyclic ring containing 2 to 4 rings.

3. The process for producing a tertiary alcohol ester according to claim 1, wherein the ring Z is norbornane ring, bornane ring, adamantane ring, bicyclooctane ring, tricyclo[5.2.1.0$^{2,6}$]decane ring or decalin ring.

4. The process for producing a tertiary alcohol ester according to claim 1, wherein the ring Z is a monocyclic or polycyclic non-aromatic ring which may have a halogen atom, an alkyl group, a hydroxyl group which may be protected by a protecting group or an amino group which may be protected by a protecting group.

5. The process for producing a tertiary alcohol ester according to claim 1, wherein $R^1$ is a halogen atom or a $C_{1-4}$ alkoxy group.

6. The process for producing a tertiary alcohol ester according to claim 1, wherein $R^2$ is a $C_{1-6}$ alkyl group, a $C_{3-12}$ cycloalkyl group or a $C_{6-20}$ aryl group.

7. The process for producing a tertiary alcohol ester according to claim 1, wherein $R^3$ is a hydrocarbon group having a polymerizable unsaturated group.

8. The process for producing a tertiary alcohol ester according to claim 1, wherein $R^3$ is vinyl group, 1-propenyl group or isopropenyl group.

9. The process for producing a tertiary alcohol ester according to claim 1, wherein the organometallic compound represented by formula (3) is an organic titanium compound, an organic magnesium compound, or an organic lithium compound.

10. The process for producing a tertiary alcohol ester according to claim 1, wherein the organometallic compound represented by formula (3) is at least one selected from the group consisting of dimethyldiisopropoxytitanium, methyl magnesium bromide, ethyl magnesium bromide, butyl magnesium bromide, methyl lithium and butyl lithium.

* * * * *